(12) United States Patent
Gunstream et al.

(10) Patent No.: US 8,084,260 B2
(45) Date of Patent: Dec. 27, 2011

(54) SPECTRAL CALIBRATION METHOD AND SYSTEM FOR MULTIPLE INSTRUMENTS

(75) Inventors: Stephen J. Gunstream, San Francisco, CA (US); Mark Oldham, Los Gatos, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 1335 days.

(21) Appl. No.: 11/286,071

(22) Filed: Nov. 23, 2005

(65) Prior Publication Data

US 2006/0138344 A1 Jun. 29, 2006

Related U.S. Application Data

(60) Provisional application No. 60/630,745, filed on Nov. 24, 2004.

(51) Int. Cl.
  *G01N 21/64* (2006.01)
  *G01N 35/00* (2006.01)
  *G01N 21/93* (2006.01)

(52) U.S. Cl. ............. 436/8; 422/63; 422/64; 422/65; 422/67; 422/82.05; 422/82.09; 436/43; 436/46; 436/47; 436/172; 702/19; 702/22; 702/31; 702/32

(58) Field of Classification Search ............. 422/63–67, 422/82.05, 82.08–82.09; 436/8, 43, 46–47, 436/94, 172; 702/19–20, 22, 27–28, 31–32
See application file for complete search history.

(56) References Cited

U.S. PATENT DOCUMENTS

| | | | | |
|---|---|---|---|---|
| 4,032,975 A | * | 6/1977 | Malueg et al. | 358/482 |
| 4,794,450 A | * | 12/1988 | Saito et al. | 348/61 |
| 4,968,148 A | * | 11/1990 | Chow et al. | 356/427 |
| 5,072,382 A | * | 12/1991 | Kamentsky | 382/133 |
| 5,073,029 A | * | 12/1991 | Eberly et al. | 356/432 |
| 5,112,134 A | * | 5/1992 | Chow et al. | 356/427 |
| 5,252,818 A | * | 10/1993 | Gerlach et al. | 250/208.1 |
| 5,265,169 A | * | 11/1993 | Ohta et al. | 382/130 |
| 5,389,555 A | * | 2/1995 | Watanabe et al. | 436/164 |
| 5,766,875 A | * | 6/1998 | Hafeman et al. | 435/29 |
| 5,854,684 A | * | 12/1998 | Stabile et al. | 356/440 |
| 5,861,256 A | * | 1/1999 | Glass et al. | 435/6 |
| 6,103,479 A | * | 8/2000 | Taylor | 506/14 |
| 6,317,207 B2 | * | 11/2001 | French et al. | 356/317 |
| 6,348,965 B1 | * | 2/2002 | Palladino et al. | 356/243.1 |
| 6,441,973 B1 | * | 8/2002 | Ramm et al. | 359/778 |
| 6,496,309 B1 | * | 12/2002 | Bliton et al. | 359/618 |
| 6,518,068 B1 | * | 2/2003 | Gambini et al. | 436/50 |

(Continued)

OTHER PUBLICATIONS

Chapman, G. B., II et al, Applied Spectroscopy 1978, 32, 46-53.*

(Continued)

*Primary Examiner* — Arlen Soderquist (57) ABSTRACT

Implementations of the present invention describe an apparatus for generating calibration factors for a spectral detector instrument. The calibration factors are derived from a calibration plate containing one or more spectral species in each well of the calibration plate. Each well is then exposed to an excitation source that causes the one or more spectral species in each of the wells to fluoresce. The signal response is measured and associated with each spectral species at each different well position in the calibration plate. Next, the measured signal response from each spectral species at each well position in the calibration plate is compared with a predetermined signal response for each spectral species. The results of this comparison can be used to determine a calibration factor for each well and spectral species to compensate for the difference between the measured signal response and the predetermined signal response.

18 Claims, 7 Drawing Sheets

U.S. PATENT DOCUMENTS

| | | | | |
|---|---|---|---|---|
| 6,556,299 | B1* | 4/2003 | Rushbrooke et al. | 356/417 |
| 6,586,257 | B1* | 7/2003 | Vuong | 436/165 |
| 6,589,788 | B1* | 7/2003 | Potyrailo et al. | 436/37 |
| 6,813,615 | B1* | 11/2004 | Colasanti et al. | 706/46 |
| 6,905,881 | B2* | 6/2005 | Sammak et al. | 436/172 |
| 7,435,602 | B2* | 10/2008 | Gunstream et al. | 436/172 |
| 2002/0070349 | A1* | 6/2002 | Hoyt | 250/458.1 |
| 2002/0098588 | A1* | 7/2002 | Sammak et al. | 436/8 |
| 2004/0208350 | A1* | 10/2004 | Rea et al. | 382/128 |
| 2005/0095665 | A1* | 5/2005 | Williams et al. | 435/34 |
| 2006/0257013 | A1* | 11/2006 | Ramm et al. | 382/133 |
| 2006/0275847 | A1* | 12/2006 | Goodyer et al. | 435/7.32 |

OTHER PUBLICATIONS

Harrison, R. O. et al, Journal of the Association of Official Analytical Chemists 1988, 71, 981-987.*

Vesanen, M. et al, Journal of Virological Methods 1996, 59, 1-11.*

Escobar, N. I. et al, Journal of Immunological Methods 1996, 196, 97-99.*

Ray, K. G. et al, Applied Spectroscopy 1997, 51, 108-116.*

Grundmann, H. J. et al, Journal of Clinical Microbiology 1997, 35, 3071-3077.*

Liu, Y. et al, Analytical Biochemistry 1999, 267, 331-335.*

Lin, K. et al, BioTechniques 1999, 26, 318-326.*

Abriola, L. et al, Journal of Biomolecular Screening 1999, 4, 121-127.*

Bantan-Polak, T. et al, Analytical Biochemistry 2001, 297, 128-136.*

Colantuoni, C. et al, BioTechniques 2002, 32, 1316-1320.*

Paul Geladi, Bruce R. Kowalski, *Analytica Chimica Acta*, vol. 185, pp. 1-17, 1986.

Agnar Höskuldsson, *Journal of Chemometrics*, vol. 2, pp. 211-228, 1988.

Svante Wold, et al., *Chemometrics and Intelligent Laboratory Systems*, vol. 58, pp. 109-130, 2001.

Richard G. Brereton, *The Analyst*, vol. 125, pp. 2125-2154, 2000.

\* cited by examiner

SPECTRAL CALIBRATION METHOD AND SYSTEM FOR MULTIPLE INSTRUMENTS

CROSS-REFERENCE TO RELATED APPLICATIONS

This application claims priority to U.S. Provisional Application No. 60/630,745, filed Nov. 24, 2004 assigned to the assignee of the present invention entitled, "Normalization of Data in Sequencing Detection Systems", which is incorporated herein by reference.

INTRODUCTION

Real-time polymerase chain reaction (real-time PCR) instruments use a cycle threshold (Ct) as an indication of the gene expression associated with an underlying target. The gene expression of a specific sample polynucleotide provides an indication of its underlying genes. Generally, real-time PCR obtains Ct value measurements by performing a thermal cycle and detecting a corresponding change in the signal emitted from a fluorescent dye or spectral species. Consequently, accurately determining the Ct value is an important part of obtaining more accurate experimental results and quantification of the gene expression for the target of interest.

Ct variability is also a factor to consider if gene expression for a target is to be accurately measured and compared. In some cases, Ct variability may occur as components on an individual instrument are broken-in or wear through normal usage over time. Other cases of Ct variability may arise when multiple instruments are used to measure the gene expression for a given target. Yet another set of factors contributing to Ct variability may include: pipeting errors, instrument sensitivity drift, different thresholds and different baselines.

A number of diagnostic assays attempt to control the Ct values using a baseline value and threshold for a particular assay. The baseline value offsets background signals resulting from fluorescence levels that may fluctuate due to changes in the reaction medium. Generally, the baseline value is established early in a reaction and prior to the detection of a change in fluorescent signal of the target sample. The fluorescence levels detected at this point can readily be attributed to background signal. Once the baseline is set, the threshold is typically set at some number of standard deviations above the mean baseline fluorescence. Further additional adjustments ensure the threshold is in the exponential phase of the amplification curve, as well as meeting other criteria. This approach works well when the spectral sensitivity in the instrument does not vary over time or across instruments.

Unfortunately, the baseline approach above tends not to work well in experiments performed over time on a single instrument or on multiple instruments. These instruments tend to have various spectral sensitivities and report a non-uniform spectral response. Some of the more notable factors causing spectral non-uniformity include but are not limited to different optics and optical paths, different sensitivities across the spectra and varying usage or age of the instruments. Even in the same instrument, spectral non-uniformity may arise from light source characteristics changing over time, paths of light being received differently at various well positions in a plate, variations in the optical covers used to seal the wells in the plate and many other reasons. Overall, spectral non-uniformity makes it difficult to achieve reproducible Ct values and compare results from one or multiple instruments running experiments over any length of time.

It is desirable to reduce the effects of spectral non-uniformity that occur between different instruments or the same instrument measuring spectral species over time.

BRIEF DESCRIPTION OF THE DRAWINGS

The skilled artisan will understand that the drawings, described below, are for illustration purposes only. The drawings are not intended to limit the scope of the present teachings in any way.

SUMMARY

Aspects of the present invention describe an apparatus for generating calibration factors for a spectral detector instrument. The calibration factors are derived from a calibration plate containing one or more spectral species in each well of the calibration plate. Each well is then exposed to at least one excitation source that causes the one or more spectral species in each of the wells to fluoresce. The signal response is measured and associated with each spectral species at each different well position in the calibration plate. Next, the measured signal response from each spectral species at each well position in the calibration plate is compared with an expected or predetermined signal response for each spectral species. The results of this comparison can be used to determine a calibration factor for each well and spectral species to compensate for the difference between the measured signal response and the expected signal response.

Other aspects of the present invention describe a method of calibrating a spectral detector instrument with a calibration factor associated with each well of a plate. The spectral detector initially receives the plate containing one or more unknown targets and spectral species in each well of a plate. At least one excitation source exposes each well and causes the spectral species to fluoresce in correlation to the presence of a particular target. The fluorescent signal measurements are received from the spectral species in different well positions of the plate. The calibration factors for each well and spectral species combination derived from a calibration plate adjust the measured signal values according to the corresponding well position on the plate.

These and other features of the present teachings are set forth herein.

DESCRIPTION

Figure 1:
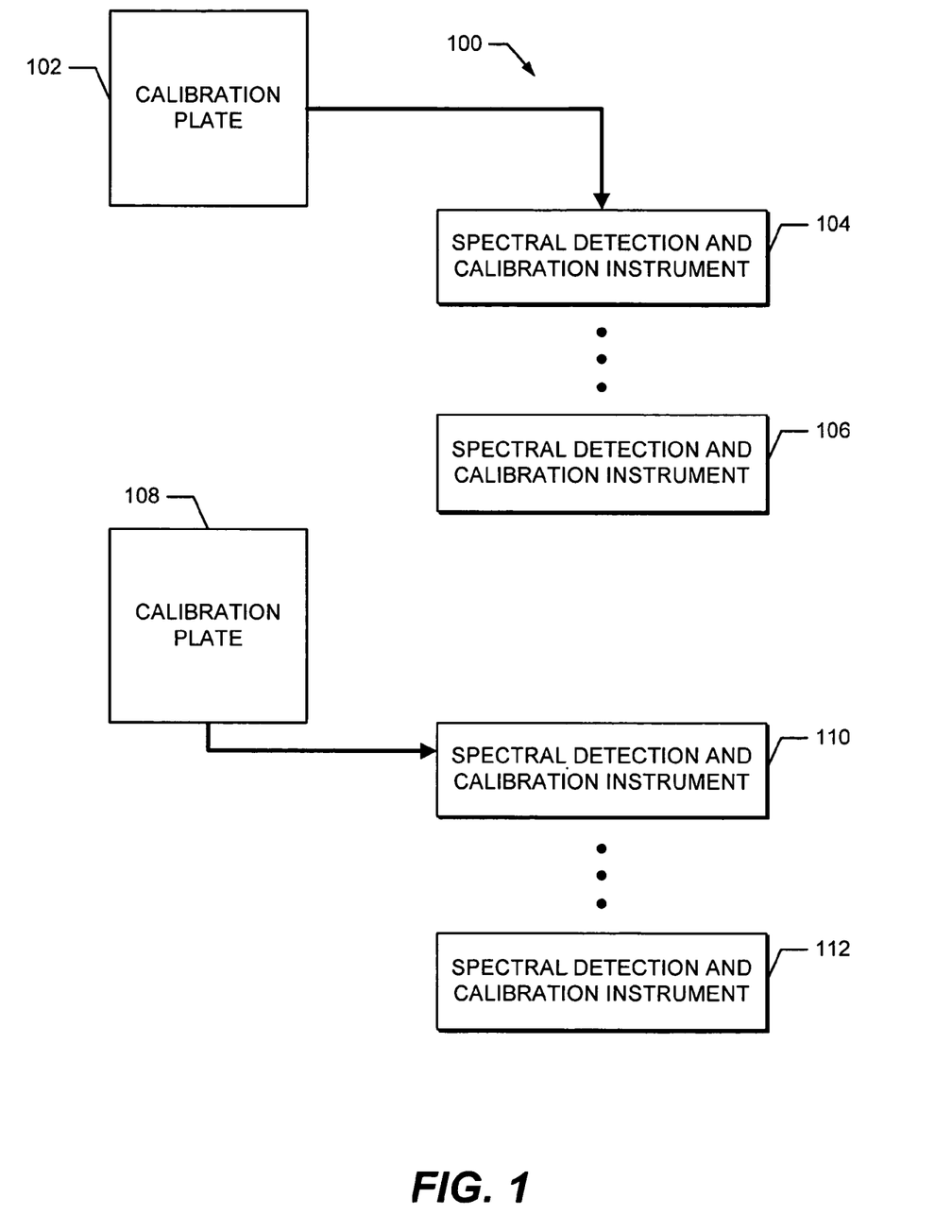
FIG. 1 is a schematic illustrating a system for spectral detection and calibration in accordance with implementations of the present invention.

FIG. 1 is a schematic illustrating a system for spectral detection and calibration in accordance with some implementations of the present invention. System 100 includes a calibration plate 102, spectral detection and calibration instrument 104 through 106, a calibration plate 108 and spectral detection and calibration instruments 110 through 112. For example, each spectral detection and calibration instrument generally includes a spectral detector capable of identifying certain spectral species emitted from a sample and a calibration component operable in accordance with various aspects of the present invention to calibrate the spectral information gathered. Calibration plate 102 includes one or more spectral species heat or pressure or mechanically sealed in multiple wells by a seal or cap. Similarly, calibration plate 108 contains essentially the same combination of spectral species sealed likewise in the same number of wells.

By carefully manufacturing calibration plate 102, the expected signal emitted from the spectral species in calibration plate 102 can be determined in advance. This requires accurately specifying the combination of spectral species inserted in each well of calibration plate 102. Detected variations from the expected signal during calibration are presumed to be peculiar to the instrument and the well position and capable of compensation using calibration factors as described in further detail later herein. For example, a predetermined mixture of five different unquenched dyes inserted in each well fluoresce a predetermined signal in the presence of certain wavelengths of light. In the case of real-time PCR instruments, the five different dyes, reporters or reagents inserted in each well can be selected from a set including: FAM, SYBR Green, VIC, JOE, TAMRA, NED CY-3, Texas Red, CY-5, Hex, ROX (passive reference) or any other fluorochrome. Alternate implementations may use greater or fewer than five dyes depending on the specific instrument and measurements being made. While fluorescence is one source of signal described in detail herein, aspects of the present invention can also be applied and used in conjunction with instruments measuring phosphorescence, chemiluminescence and other signal sources.

An arbitrary number of spectral detection and calibration instruments 104 through 106 may use the same calibration plate 102 to detect various spectral species. Each of spectral detection and calibration instrument 104 through 106 is likely to detect different spectral species in calibration plate 102 due to differences in optics, different quantum efficiencies of detectors/cameras sampling the signals produced, varying sensitivities to spectra between instruments and other variations between the instruments.

Even the same spectral detection and calibration instrument 104 may detect different spectral species from calibration plate 102 taken at subsequent time intervals. These differences can be attributed to wear of the instrument and small changes in the spectral sensitivity of the same detector over time, degradation of an excitation source in the detector instrument or any other number of changes to the instrument and/or the environment that may occur over time. Spectral detection and calibration instrument 104 also is likely to detect a different quantification of spectral species from well to well in calibration plate 102 due to the different light paths to each well and variations in the optical seals used to cap each well.

Aspects of the present invention can be used to create a set of calibration factors for each of spectral detection and calibration instrument 104 through 106. These calibration factors accommodate for the signal differences between the spectral species measured by each instrument and the predetermined or known signal expected from one or more spectral species included in each well of calibration plate 102. These calibration factors are not only useful to compensate for differences between several instruments or the same instrument over time but also for the spectral variation occurring from well-to-well. For example, aspects of the present invention measure spectral response for each well and create calibration factors corresponding to each well. In some implementations, the calibration factor for an instrument can be applied in real-time to correct the signal data being detected while other implementations tend to correct the signal data being detected using the calibration factor in one or more post-processing operations.

The additional calibration plate 108 depicted in FIG. 1 indicates that more than one calibration plate can be used to calibrate spectral detection and calibration instrument 104 through 106 and spectral detection and calibration instrument 110 through 112. Precisely manufacturing calibration plate 102, calibration plate 108 and other calibration plates to contain the same combination of spectral species in each well of the plate makes such an approach to calibration possible. Consequently, spectral detection and calibration instruments 104 through 106 can be calibrated to work with spectral detection and calibration instruments 110 through 112 using either calibration plate 102 and/or calibration plate 108. In real-time PCR, this enables multiple real-time PCR instruments calibrated in accordance with implementations of the present invention to work together even though the instruments may have different spectral sensitivities and spectral response to the spectral species.

Figure 2:
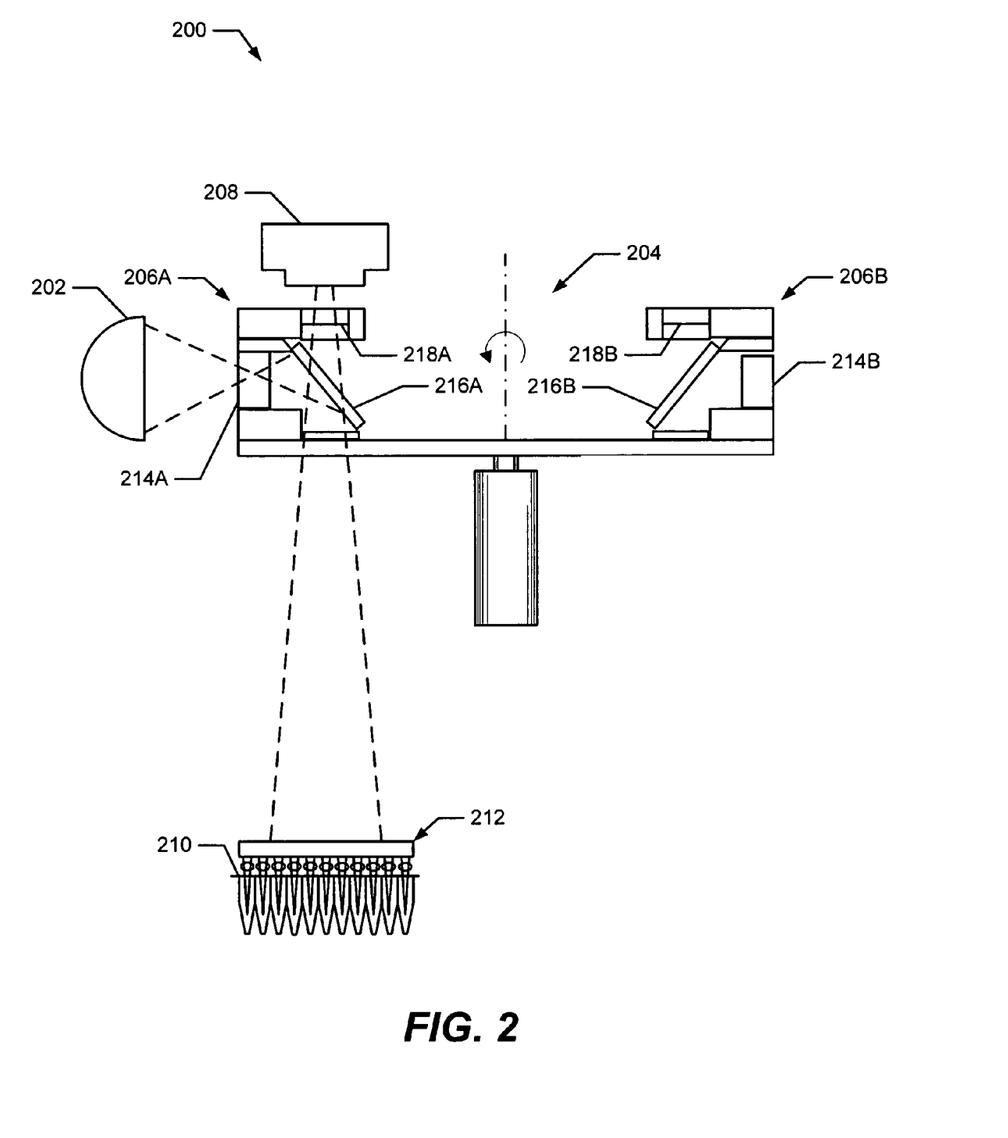
FIG. 2 is a schematic illustration of a system used for fluorescent signal detection in accordance with implementations of the present invention.

FIG. 2 is a schematic illustration of a system used for fluorescent signal detection in accordance with implementations of the present invention. Detection system 200 is an example of spectral detection and calibration instrument 104 previously described in FIG. 1. Detection system 200 can be used with real-time PCR processing in conjunction with aspects of the present invention. As illustrated, detection system 200 includes a light source 202, a filter turret 204 with multiple filter cubes 206, a detector 208, a microwell tray 210 and well optics 212. A first filter cube 206A can include an excitation filter 214A, a beam splitter 216A and an emission filter 218A corresponding to one spectral species selected from a set of spectrally distinguishable species to be detected. A second filter cube 206B can include an excitation filter 214B, a beam splitter 216B and an emission filter 218B corresponding to another spectral species selected from the set of spectrally distinguishable species to be detected.

Light source 202 can be a laser device, Halogen Lamp, arc lamp, Organic LED, an LED lamp or other type of excitation source capable of emitting a spectra that interacts with spectral species to be detected by system 200. In this illustrated example, light source 202 emits a broad spectrum of light filtered by either excitation filter 214A or excitation filter 214B that passes through beam splitter 216A or beam splitter 216B and onto microwell tray 210 containing one or more spectral species. Further information on light sources and overall optical systems can found in U.S. Patent Application 20020192808 entitled "Instrument for Monitoring Polymerase Chain Reaction of DNA", by Gambini et al. and 200438390 entitled "Optical Instrument Including Excitation Source" by Boege et al. and assigned to the assignee of the present case.

Light emitted from light source 202 can be filtered through excitation filter 214A, excitation filter 214B or other filters that correspond closely to the one or more spectral species. As previously described, each of the spectrally distinguishable species may include one or more of FAM, SYBR Green, VIC, JOE, TAMRA, NED, CY-3, Texas Red, CY-5, Hex, ROX (passive reference) or any other fluorochromes that emit a signal capable of being detected. In response to light source 202, the target spectral species and selected excitation filter, beamsplitter and emission filter combination provide the largest signal response while other spectral species with less signal in the bandpass region of the filters contribute less signal response. Multicomponent analysis is typically used to determine the concentration of the individual species according to their respective contribution to the emitted spectra. Depending on the number of excitation filters and spectral species or dyes, a series of linear equations as indicated in Equation 1 below are used to perform the multicomponent analysis:

$$\vec{P}_{aw} \cdot \vec{D}_{calibrate} = \vec{S}_{aw} \qquad \text{Equation 1}$$

Where:

$\vec{P}_{aw}$ is a 'pure dye' matrix of $n_c \times n_p$ for 'all wells' (aw) in a tray.

$n_c$ is the number of detector channels/filters being detected by the instrument.

$n_p$ is the number of spectral species being detected by the instrument.

$\vec{D}_{calibrate}$ is a species concentration column vector for each $n_p$ spectral species used for calibration.

$\vec{S}_{aw}$ is a column vector corresponding to a spectral response. measured at a particular wavelength for 'all wells' (aw) in the tray.

The initial pure dye matrix $\vec{P}_{aw}$ contains pure-component linear response constants representing the individual contribution of each of the $n_p$ species detected using a different filter from the detector. The constant values in pure dye matrix $\vec{P}_{aw}$ are determined by measuring the pure-component response detected by the detector with different filter combinations. For example, $\vec{P}_{aw}$ can be detected using a single measurement of the signal response from a pure dye in all wells or averaging the signal response of a pure dye from a collection of wells in the tray. By normalizing the values in $\vec{P}_{aw}$, the sum of the values detected using each filter adds up to unity.

Species concentration column vector $\vec{D}_{calibrate}$ provides the concentration of each spectral species in a mixture and inserted into each well of a calibration tray. As will be described in further detail later herein, the concentration of each spectral species indicated in column vector $\vec{D}_{calibrate}$ is known in advance and is the same in each well throughout the calibration tray or plate. Using known concentration levels of each species facilities generating the appropriate calibration factors to compensate for spectral non-uniformity associated with the instrument and well location in the tray.

$\vec{S}_{aw}$ is a column vector corresponding to a spectral response measured at a particular wavelength from all wells in the calibration tray. For calibration, each well is presumed to have the same concentration of species and therefore is attributed the same measured spectral response $\vec{S}_{aw}$. The spectral values stored in $\vec{S}_{aw}$ is later compared with the measured spectral response from different well positions and used to generate a calibration factor for the spectral response in the well position.

For example, a target spectral species passing through a selected excitation filter may emit a signal detected as 850 units while the other two spectral species passing through the same filter may only be detected as 100 units and 50 units respectively. Each coefficient in the pure dye calibration matrix $\vec{P}_{aw}$ represents the contribution of each spectral species to the overall spectral response detected for a given filter and dye combination. Accordingly, the pure dye matrix of coefficients $\vec{P}_{aw}$ multiplied by the concentration of each spectral species $\vec{D}_{calibrate}$ results in the measured signal detected $\vec{S}_{aw}$.

It also possible to derive the spectral species concentration $\vec{D}_{calibrate}$ through a modification of Equation 1 above and depicted by the linear relationship of Equation 2 below using $\vec{S}_{aw}$. When a spectral measurement $\vec{S}_w$ is taken from different individual well positions within a tray, it is necessary to adjust the results using a calibration factor. For example, aspects of the present invention have determined that a dye-based calibration factor $\vec{Cf}_{w-dye}$ as depicted in Equation 2 below can be used to correct for spectral non-uniformity from a particular instrument when detecting spectral response from different wells in a plate.

$$\vec{D}_{calibrate} = (\vec{P}_{aw}^{-1}) \vec{S}_{aw} = (\vec{P}_{aw}^{-1}) \vec{S}_w \cdot \vec{Cf}_{w-dye} \qquad \text{Equation 2}$$

Where:

$\vec{S}_w$ is a column vector corresponding to a spectral response. measured at a particular wavelength for 'a well' (w) in the tray.

$\vec{Cf}_{w-dye}$ is a column vector of calibration factors for each well derived with a dye-filter combination that matches an assay.

Equation 3 below is one method of determining the dye-based calibration factor $\vec{Cf}_{w-dye}$ through a linear equation.

$$\vec{Cf}_{w-dye} = (\vec{P}_{aw} \cdot \vec{D}_{calibrate}) \cdot \vec{S}_w^{-1} \qquad \text{Equation 3}$$

$\vec{P}_{aw}$ is a 'pure dye' matrix of $n_c \times n_p$ for 'all wells' (aw) in a tray.

Spectral non-uniformity in an instrument occurs for several reasons and notably varies from well to well in the tray. The dye-based calibration factor of Equation 3 can be used to correct spectral response for different dyes and different wells in a tray. Aspects of the present invention modify a detected spectral response in the dye-based calibration approach by a calibration factor $\vec{Cf}_{w-dye}$ to correct the spectral measurement. By factoring this calibration factor $\vec{Cf}_{w-dye}$ into the relationship, a deconvolved spectral response accurately reflects the spectral response of the underlying species being measured in different well locations on a tray and across multiple instruments.

This aforementioned approach to correcting spectral response using calibration factor $\vec{Cf}_{w-dye}$ can be referred to as 'a dye-based calibration'. This solution uses a combination of spectral species that match the assay from the experiment being performed. Each calibration factor of $\vec{Cf}_{w-dye}$ corrects an underlying species deconvolved using the pure dye matrix $\vec{P}_{aw}$.

Implementing the dye-based calibration solution may be time consuming and cost-prohibitive. The calibration factors $\vec{Cf}_{w\text{-}dye}$ in this approach are derived from an instrument having filters and dyes that match the particular assay for the experiment. For example, a dye-based calibration solution needs an instrument with a set of three filters to match the three spectral species of a three-dye assay. Larger assays using four or more different dyes would require the generation of a new pure dye matrix $\vec{P}_{aw}$ and a set of calibration factors $\vec{Cf}_{w\text{-}dye}$ for each well. Instead of three filters, these larger assays of four or more different dyes would require an instrument having four or more filters corresponding to these particular dyes.

While the dye-based calibration approach may provide a more accurate solution, an alternate "filter-based approach" also provides high quality results yet does not require an instrument with specifically matching filters and dyes. Under the filter-based approach, a pure dye matrix $\vec{P}_{aw}$ for a set of spectral species can be used even though a calibration factor $Cf_{w\text{-}filter}$ was derived for a different spectral species. The pure dye matrix $\vec{P}_{aw}$ can also be used with assays of greater or fewer than $n_p$ spectral species or $n_c$ filters that were originally used to derive the calibration factor $Cf_{w\text{-}filter}$.

In the filter-based approach, a calibration factor $Cf_{w\text{-}filter}$ is derived directly from the signal response detected without deconvolving individual spectral species. Essentially, calibration factor $Cf_{w\text{-}filter}$ corrects for the non-uniform spectral response received from different well positions $S_w$ compared with the composite signal response received from all the wells $S_{aw}$. Equation 4 below expresses the relationship between the signal response received from all the wells $S_{aw}$ and the signal response from a particular well $S_w$ using calibration factor $Cf_{w\text{-}filter}$.

(1) $S_{aw} = S_w \cdot Cf_{w\text{-}filter}$ (2) $S_{aw} \cdot S^{-1}_w = Cf_{w\text{-}filter}$   Equation 4

Where:
$Cf_{w\text{-}filter}$ is a calibration factor for each well derived using a dye-filter combination that may not match the filters or dye used in an assay or experiment.

The filter-based solution uses a spectral response obtained from all wells in a tray $S_{aw}$ as compared with the spectral response obtained directly from an individual well $S_w$. Unlike the dye-based approach previously mentioned, the calibration factor $Cf_{w\text{-}filter}$ in the filter-based approach is not specific to individual spectral species but used to correct the overall spectral response for each well in the tray and instrument together. Accordingly, it is not required that the dyes and filters used by the instrument to generate $Cf_{w\text{-}filter}$ match the dyes and consequently the filters used by the assay in the individual experiment. Alternatively, it is understood that while the signal response can be measured from a set of wells in a tray that this measurement could instead be set to a predetermined value evaluated more broadly from a larger set of instruments and/or trays of dye. For example, this approach could be labeled as a standard spectral response instead of a measurement made from a composite of all the wells.

Calibration factor $Cf_{w\text{-}filter}$ is applied to the pure dye matrix $\vec{P}_{aw}$. Instead of using $\vec{P}_{aw}$, the filter-based calibration approach uses the modified pure dye matrix $\vec{P}_{aw\text{-}filter}$ to deconvolve each spectral species from a sample using multi-component analysis, as indicated in Equation 5 below:

(1) $\vec{P}_{aw\text{-}filter} = \vec{P}_{aw} \cdot Cf^{-1}_{w\text{-}filter}$ (2) $\vec{P}_{aw\text{-}filter} \cdot \vec{D}_w \cong \vec{S}_w$ (3) $\vec{D}_w \cong \vec{P}^{-1}_{aw\text{-}filter} \cdot \vec{S}_w$   Equation 5

Where:
$\vec{S}_w$ is a signal response vector for the spectral species in an experimental sample $\vec{D}_w$ at a particular wavelength and corrected using a filter-based calibration factor $Cf_{w\text{-}filter}$.

$\vec{D}_w$ is an experimental sample of unknown species concentrations in a well w of a tray having many different wells.

$Cf_{w\text{-}filter}$ is a filter-based calibration factor.

$\vec{P}_{aw\text{-}filter}$ is a pure dye matrix corrected using a filter-based calibration factor and used to deconvolve unknown species concentrations.

Referring to FIG. 2, microwell tray 210 can be a calibration plate designed in accordance with implementations of the present invention containing one or more unquenched dyes or reporters useful in calibrating system 200. Alternatively, quenched dyes could also be used but would require higher levels of concentration to work properly. Each microwell tray 210 can include a single well or any number of wells however, typical sets include 96-wells, 384-wells and other multiples of 96-wells. Of course, many other plate configurations having different multiples of wells other than 96 can also be used. If microwell tray 210 includes multiple wells then the different optical paths to each of the wells in microwell tray 210 from detector 208 may contribute to producing a non-uniform spectral response.

The particular combination of dyes is sealed in microwell tray 210 using heat and an adhesive film to ensure they do not evaporate or become contaminated. Due to uneven melting of the film upon sealing, the optical transmission of light may vary from well-to-well in microwell tray 210 depending on the thickness of the seal, angle and position of light passing through the heat sealed covers, different optical paths and other potential variations between the wells. As previously mentioned and described in further detail later herein, aspects of the present invention generate a calibration factor for each different well position in microwell tray 210 to accommodate for these and other variations. Calibration factors generated for each well also compensate for variation in spectral response due to the many different angles of entry for the light in the various wells in microwell tray 210 as well as the angles of light through the various filters.

Detector 208 receives the signal emitted from spectral species in microwell tray 210 in response to light passing through the aforementioned filters. Detector 208 can be any device capable of detecting fluorescent light emitted from multiple spectrally distinguishable species in the sample. For example, detector 208 can be selected from a set including a charge coupled device (CCD), a charge induction device (CID), a set of photomultiplier tubes (PMT), photodiodes and a CMOS device. Information gathered by detector 208 can be processed in real-time in accordance with implementations of the present invention or through subsequent post-processing operations to correct for the non-spectral uniformity.

Figure 3:
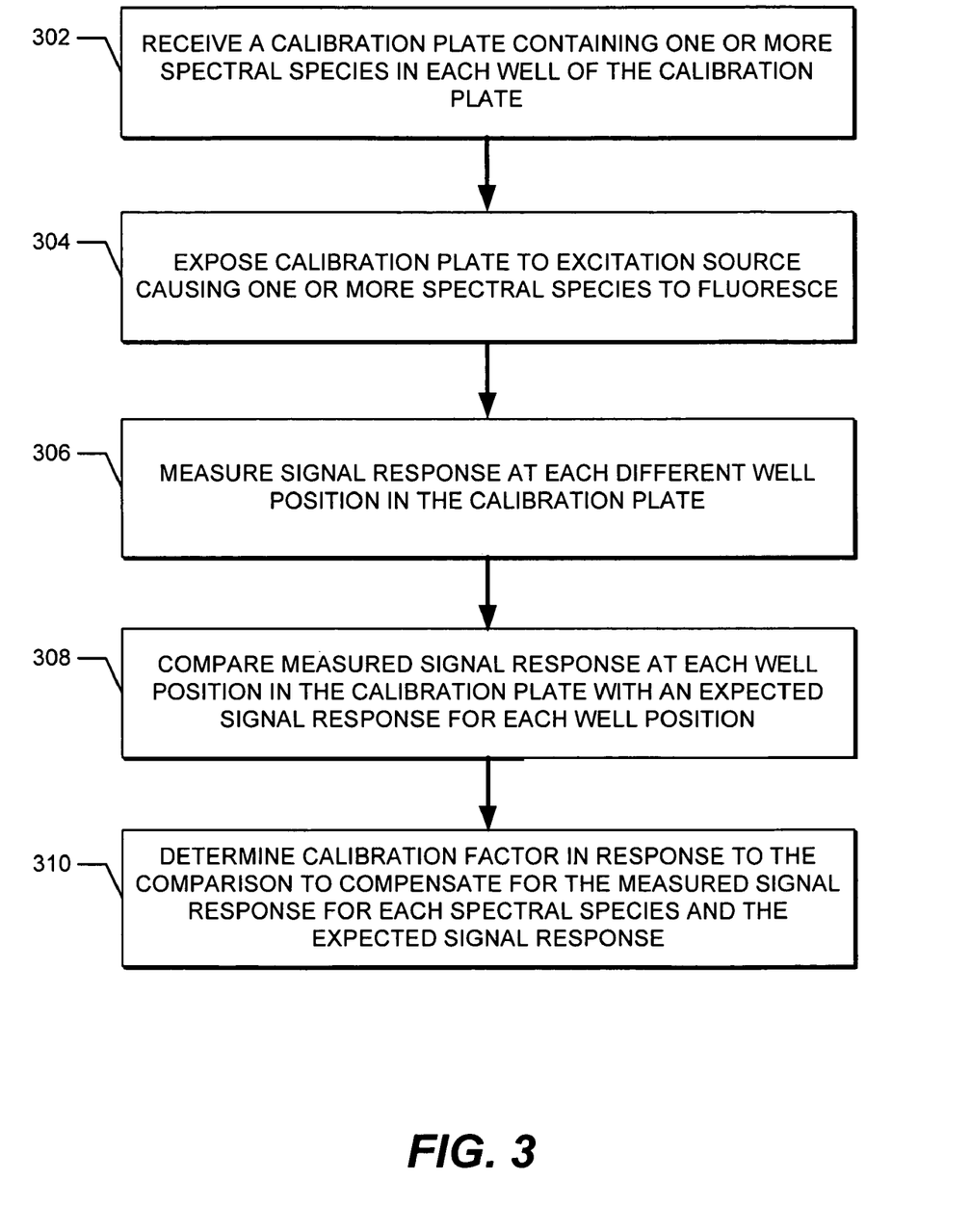
FIG. 3 is a flowchart diagram of operations performed in accordance with implementations of the present invention to calibrate an instrument detecting a spectral response from a plate of spectral species.

FIG. 3 is a flowchart diagram of operations performed to calibrate an instrument detecting a spectral response from a plate of spectral species. A single pass of the flowchart diagram steps is provided even though the steps are performed repeatedly for each filter from a group of filters used by the instrument. Initially, a calibration plate containing one or more spectral species is inserted into the instrument (302). The calibration plate is precision manufactured to contain a predetermined combination of dyes, reporters or fluorochromes in each well and represented as species concentration $\vec{D}_{calibrate}$.

Next, implementations of the present invention expose the calibration plate to an excitation source causing one or more spectral species to fluoresce (304). As previously described, the excitation sources can include lasers, LEDs and any other source of providing broad range spectrum of light. The type of excitation source used in the calibration step should substantially match the excitation source to be used during diagnostics to reflect the light path and optics used in the instrument. Further, it may be advisable to perform a new calibration especially if the excitation source has degraded over time, been replaced or even repositioned as these types of events may affect the optical path and introduce other variations that affect spectral non-uniformity. Equation 6 represents a signal response detected when measuring the signal response from the spectral species in calibration plate $\vec{D}_{calibrate}$.

$$\vec{P}_{aw} \cdot \vec{D}_{calibrate} = \vec{S}_{aw} \qquad \text{Equation 6}$$

Once exposed, various implementations of the present invention measure the signal response associated with each spectral species at each different well position in the calibration plate (306). The different well positions in the calibration tray and other factors may cause the detector to report non-uniform spectra even though the same combination of spectral species has been stored in each well. $\vec{S}_w$ depicts the measurement of the signal response for a given well and species compared with $\vec{S}_{aw}$ which indicates the spectral response for all wells.

Implementations of the present invention compare measured signal response for each well position in the calibration plate with an expected signal response for each well position (308). Using the dye-based approach, aspects of the present invention deconvolve using a set of known dye concentrations $\vec{D}_{calibrate}$ and pure-dye matrix $\vec{P}_{aw}$ to obtain an expected spectral response $\vec{S}_{aw}$ according to Equation 7 below:

$$\vec{P}_{aw} \cdot \vec{D}_{calibrate} = \vec{S}_{aw} \qquad \text{Equation 7}$$

Dye-based calibration factor $\vec{C}f_{w\text{-}dye}$ in Equation 8 below is used when comparing the spectral response from all wells $\vec{S}_{aw}$ against the spectral response from individual wells $\vec{S}_w$ in the plate. Alternately a standard spectral response could be used as previously described herein above.

$$\vec{D}_{calibrate} = (\vec{P}_{aw}^{-1}) \vec{S}_{aw} = (\vec{P}_{aw}^{-1}) \vec{S}_w \cdot \vec{C}f_{w\text{-}dye} \qquad \text{Equation 8}$$

Alternatively, a filter-based approach may be used to compare the signal detected from all wells $\vec{S}_{aw}$ against the signal received from each individual well $\vec{S}_w$. However, this approach does not immediately deconvolve the species as it operates independent of the dye and/or filters used by the assay. The filter-based approach relies on the non-uniform spectral response stemming primarily from characteristics other than associated with specific dyes or spectral species. For example, variables affecting detection of spectral non-uniformity may include different optical paths, variations in the seals covering each well of the calibration plate and other optical variations in the detection system. Equation 9 below provides the relationship for comparing an expected signal received $S_{aw}$ against an actual signal received $S_w$ from each well using a filter-based calibration factor $Cf_{w\text{-}filter}$. This step and other associated steps are repeated for each of the different filters in question during this process.

$$S_{aw} = S_w \cdot Cf_{w\text{-}filter} \qquad \text{Equation 9}$$

Next, a calibration factor is determined in response to the comparison that compensates between the measured signal response for each spectral species and the expected signal response for each spectral species (310). Each well and spectral species has a calibration factor that compensates for the differences between the measured signal response and the expected signal response for each species. According to various implementations, the calibration factor for each well can be applied at various times during a calibration analysis.

The dye-based calibration approach applies a dye-based calibration factor $\vec{C}f_{w\text{-}dye}$ to the individual spectral species generated through a multicomponent analysis. The linear equation in equation 10 below provides a method for determining the dye-based calibration factor $\vec{C}f_{w\text{-}dye}$.

$$(\vec{P}_{aw} \cdot \vec{D}_{calibrate}) \cdot \vec{S}_w^{-1} = \vec{C}f_{w\text{-}dye} \qquad \text{Equation 10}$$

As an alternative, the filter-based approach applies the filter-based calibration factor $Cf_{w\text{-}filter}$ to the pure dye matrix $\vec{P}_{aw}$ associated with a particular assay. This operation modifies a pure dye matrix $\vec{P}_{aw}$ for a particular assay instead of modifying the response from individual spectral species as performed in the dye-based calibration approach. In the filter-based calibration approach, each instrument has a filter-based calibration factor $Cf_{w\text{-}filter}$ used to generate the pure dye matrix $\vec{P}_{aw\text{-}filter}$ and then deconvolve each spectral species from a sample per Equation 11.

$$\vec{P}_{aw\text{-}filter} = \vec{P}_{aw} \cdot Cf_{w\text{-}filter}^{-1} \qquad \text{Equation 11}$$

Where:

$\vec{P}_{aw\text{-}filter}$ is a pure dye matrix corrected using a filter-based calibration factor and used to deconvolve unknown species concentrations.

Figure 4:
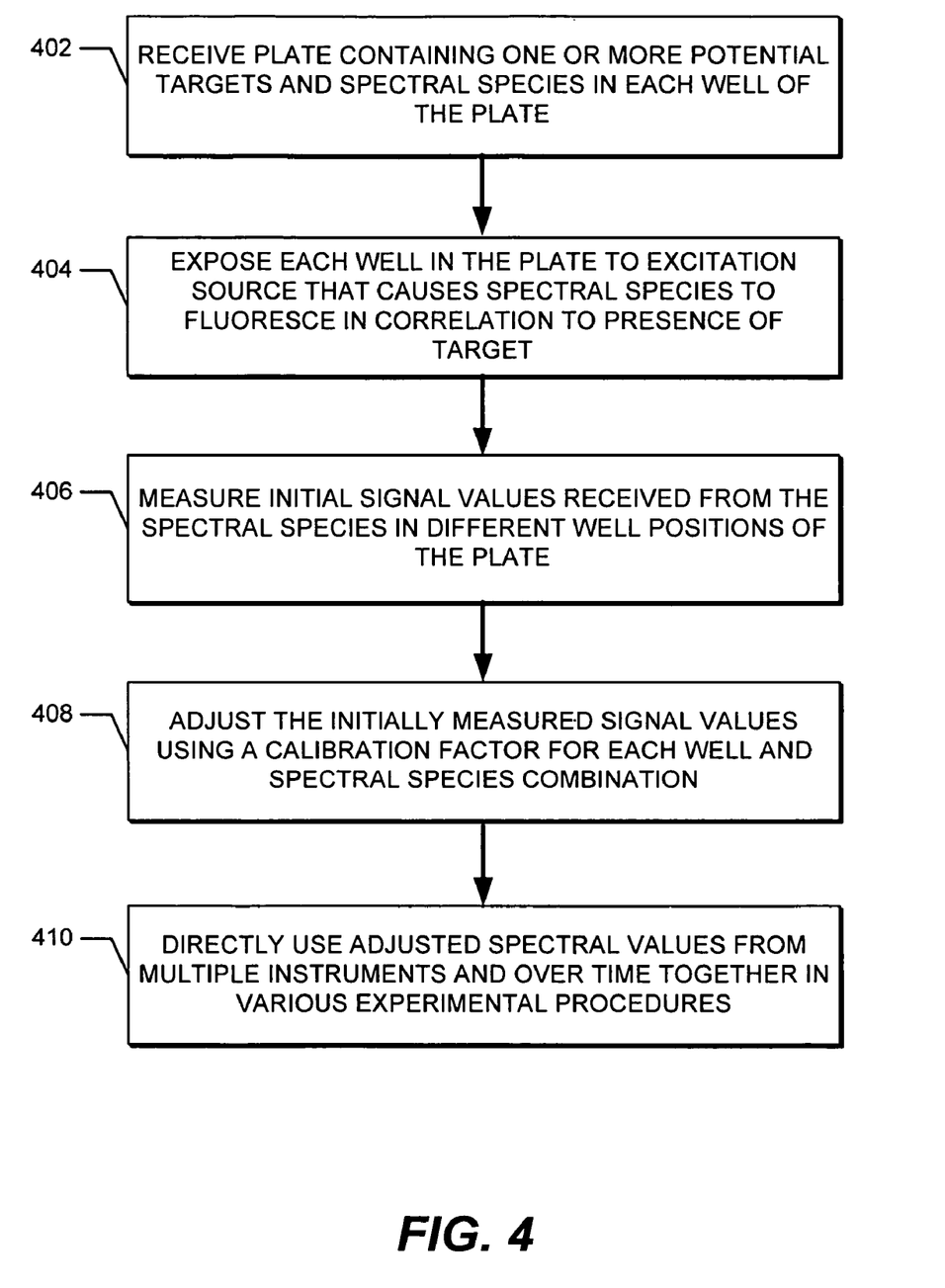
FIG. 4 provides a flowchart of the operations for applying calibration factors in accordance with implementations of the present invention.

FIG. 4 provides a flowchart of the operations for applying calibration factors in accordance with implementations of the present invention. These calibration factors correct non-uniform spectral response between different instruments and over time allowing for consistent and comparable results. For example, spectral measurements collected from different instruments calibrated using one or more calibration plates can be used together in an experiment. To use the calibration factors, an instrument receives a plate containing one or more potential targets and spectral species in each well of the plate (402). Potential targets may include polynucleotides, single nucleotide polymorphisms (SNPs), proteins and other types of targets. For example, these targets can be used in real-time PCR, allelic discrimination, sequencing and other types of analytic experiments.

Next, implementations of the present invention expose each well to an excitation source that causes one or more spectral species to fluoresce in correlation to the presence of the target (404). For brevity a single sequence of operations are indicated however these operations would generally be repeated for each filter in use by the instrument. In response to the excitation source, an instrument measures the initial spectral values from the one or more spectral species in the different well positions of the plate (406). As previously mentioned, the well position and optical seals on each plate may contribute to the non-uniform spectral response detected by an instrument over time. Variations between instruments may also contribute to the non-uniform spectral response received across instruments as well.

Implementations of the present invention therefore adjust the initially measured spectral value using a calibration factor derived for each well and spectral species combination (408).

As previously described, the calibration factors derived using a standard calibration plate design with specified ratios of species in each well of the plate. By normalizing spectral sensitivity in accordance with aspects of the present invention, multiple instruments and multiple platforms over time will operate with the same or comparable Ct values.

In the dye-based calibration approach, an experimental sample and spectral species in a well $\vec{D}_w$ is processed in an instrument resulting in a spectral response from the spectral species detected in the well $\vec{S}_w$. A corrected spectral response $\vec{S}_{w\text{-}corrected}$ for the well can be achieved through the application of the dye-based calibration factor $\vec{C}f_{w\text{-}dye}$ as indicated in Equation 12.

$$\vec{P}_{aw} \cdot \vec{D}_w = \vec{S}_w$$

$$\vec{S}_{w\text{-}corrected} = \vec{S}_w \cdot \vec{C}f_{w\text{-}dye} \qquad \text{Equation 12}$$

Where:

$\vec{S}_{w\text{-}corrected}$ is a spectral response for a species after application of a dye-based calibration factor for the particular well of a tray.

Alternatively, the filter-based calibration approach also processes an experimental sample and spectral species in a well $\vec{D}_w$. Because the pure-dye matrix $\vec{P}_{aw\text{-}filter}$ filter has been modified by the filter-based calibration factor $Cf_{w\text{-}filter}$, the resulting spectral signal response from multicomponent analysis is already corrected. As previously described, this approach is advantageous as the filter-based calibration factor $Cf_{w\text{-}filter}$ can be readily incorporated through a modification to the pure-dye matrix $\vec{P}_{aw}$ for an assay as previously indicated by Equation 11. One method of correcting the signal response from the spectral species in a well using the filter-based calibration is expressed by Equation 13 below.

$$\vec{P}_{aw\text{-}modified} \cdot \vec{D}_w = \vec{S}_{w\text{-}corrected} \qquad \text{Equation 13}$$

Where:

$\vec{S}_{w\text{-}corrected}$ is a corrected spectral response for a species after application of a filter-based calibration factor to the pure-dye matrix $\vec{P}_{aw}$.

Once the calibration factors are applied, implementations of the present invention can directly use the adjusted spectral values from multiple instruments in various experimental procedures (410).

It is also understood that calibration described herein above can also be used for absolute data measurements made from different instruments. One way to achieve this is to calibrate the instruments with the same calibration plate containing known concentration amounts. To obtain the absolute measurements, the same calibration plate can be used to calibrate different instruments and potentially in different labs. For example, the same plate may be used for all instruments in a lab and then shipped to another lab in another geographic area to calibrate the instruments and equipment in those labs.

Absolute measurements can also be obtained using multiple calibration plates and performing an additional type of calibration. Instead of making a relative calibration to the calibration plate, this calibration compares the instruments signal response and dye concentration measurement with the actual known amount of dye concentration in each well. In this case, the additional calibration requires having a known quantity of dye present in the calibration plate at manufacturing. For example, the known quantity of dye can be for a batch or precisely measured for each calibration plate. This information regarding the quantity of dye present in the calibration plate can then be used as a correction factor on an absolute basis when determining the amount of material present in a sample. For example, precise concentration amounts can be associated with each calibration plate as absolute values or as a delta or offset of concentration amounts relative to a standard concentration amount. The delta or correction in this latter case can provide a plus or minus variation of the concentration amount in the plate relative to a predetermined dye concentration standard.

In either or any other implementation, the correction factors for each dye in the calibration plate can be recorded in one or several different ways depending on the implementation. For example, the correction factors for each dye in the calibration plate can be provided with a document provided with the plate and entered manually. It may also be encoded in a barcode or embedded in a radio-frequency identification (RFID) tag with the calibration plate to be read in a more automated manner by an instrument during calibration. For example, the instrument can be equipped with a barcode scanner device or RFID reader device capable of scanning and identifying the concentration calibration information.

If the actual calibration information is not embedded in a storage device of the plate, a reference identifier read from the plate can then be used to remotely access a database or other storage area in a central repository for such information over the Internet or corporate intranet. It is possible to record the calibration data for many dyes relative to one or more other dyes in the calibration plate. Rather than keeping the absolute dye concentration information, absolute quantization can be achieved based upon measured values for one or more other dyes. This can be used to reduce the size of the data required for storage in an RFID tag/database or provide flexibility for calibrating dyes relative to each other rather than individually. For example, a calibration for various unmeasured dye concentrations could be determined using a differential measurement or factor relative to a known and measured dye present in a multiple dye calibration plate. Absolute measurements made in this manner could be determined for each instrument type and assay then incorporated using software for each dye selected by the user for a given plate. In summary, any or all of the above alternatives could be used to permit not only instrument-to-instrument relative comparisons of data but also absolute comparisons of data using multiple different calibration plates and instruments.

Figure 5:
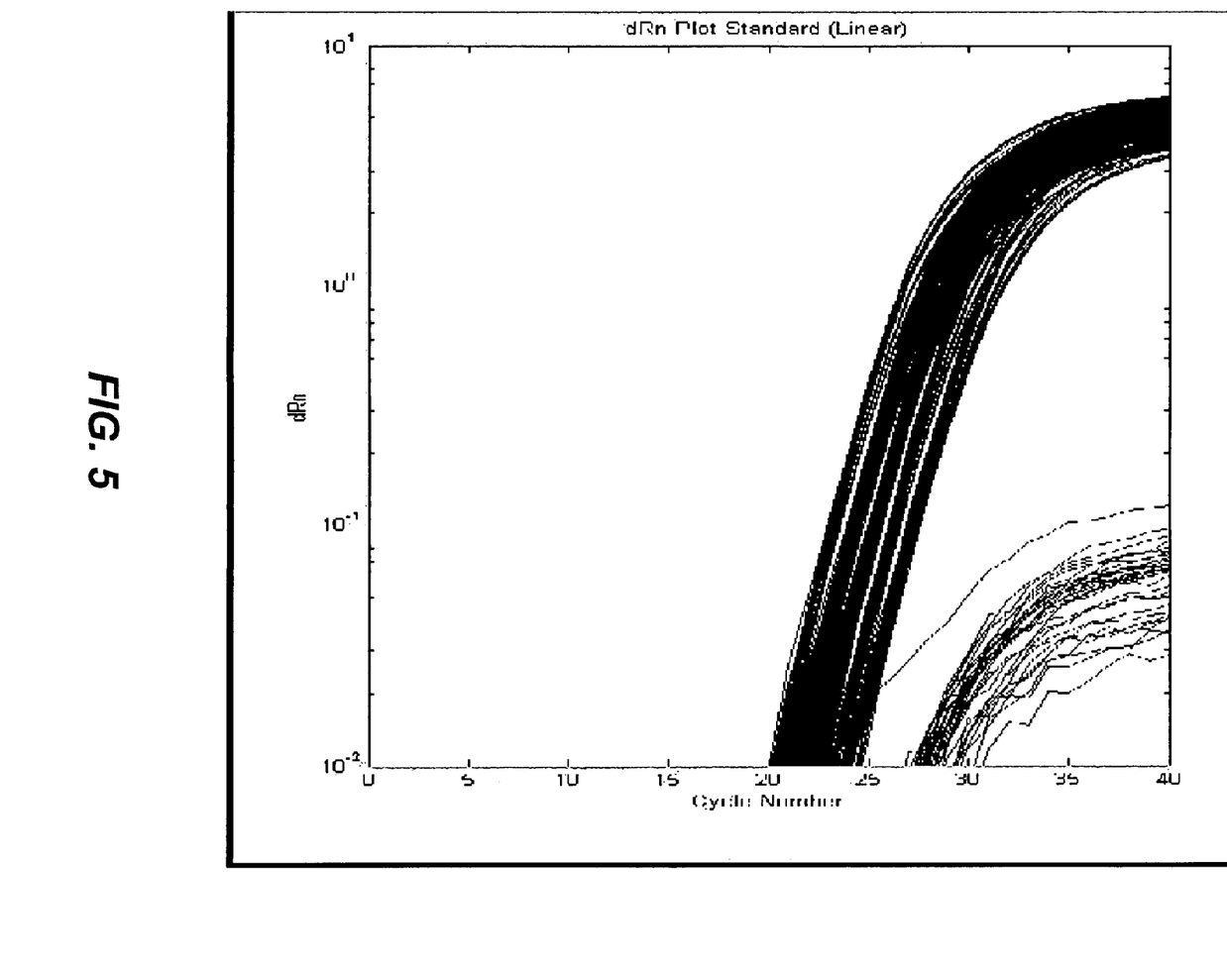
FIG. 5 is a graph illustrating a normalized amplification plot of a spectral species and corresponding cycles without calibration.

FIG. 5 is a graph illustrating a normalized amplification plot of a spectral species and corresponding cycles without calibration. Normalization using a passive reference, ROX for example is mixed into each well to normalize the variation in fluorescent signals produced to reduce the effects of volumetric variation in the sample. However, spectral sensitivity is not normalized in this amplification plot as the calibration in accordance with aspects of the present invention was not performed.

Variation is intentionally introduced by processing the same target with different dilutions using real-time PCR. These different dilutions are placed in various wells of a single tray to illustrate the effect on identifying a corresponding Ct value for each dilution. The resulting amplification plot in FIG. 5 reflects the spectral response to the reporter dye during amplification of the target. Without calibrating in accordance with implementations of the present invention, it can be observed that different dilutions of the target could otherwise not be readily distinguished as illustrated in the amplification plot.

Figure 6:
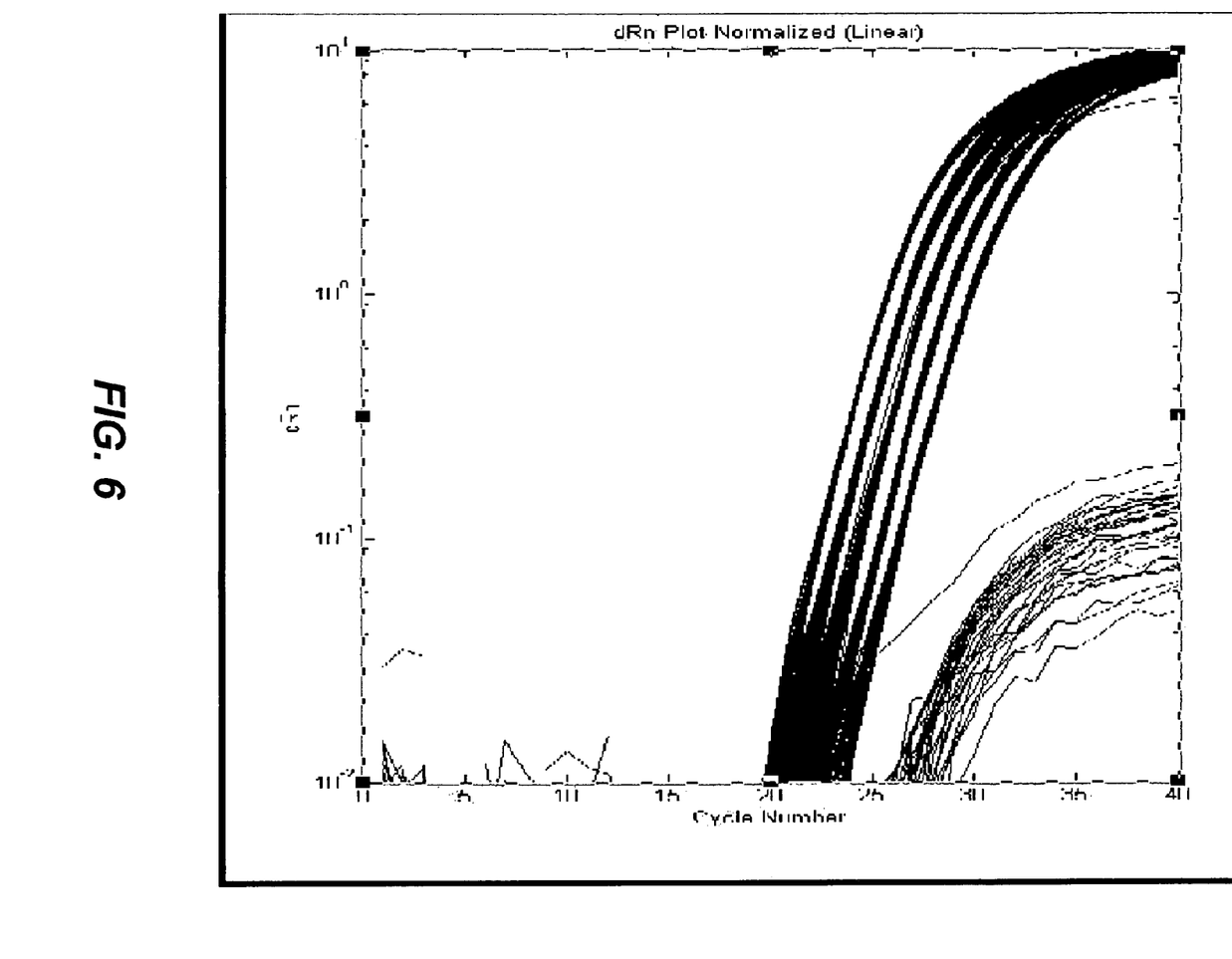
FIG. 6 is another graph illustrating a normalized amplification plot of a spectral species and corresponding cycles calibrated in accordance with implementations of the present invention.

FIG. 6 is another graph illustrating a normalized amplification plot of a spectral species and corresponding cycles calibrated in accordance with implementations of the present invention. In this graph, the plot more distinctly reflects the different dilutions being amplified even though they are placed in different well locations of the tray. Consequently, calibrating the spectral sensitivity using the calibration plate and operations described hereinabove accommodates for the non-uniform spectral response introduced by well position, optics and other variations introduced between instruments and over time.

Figure 7:
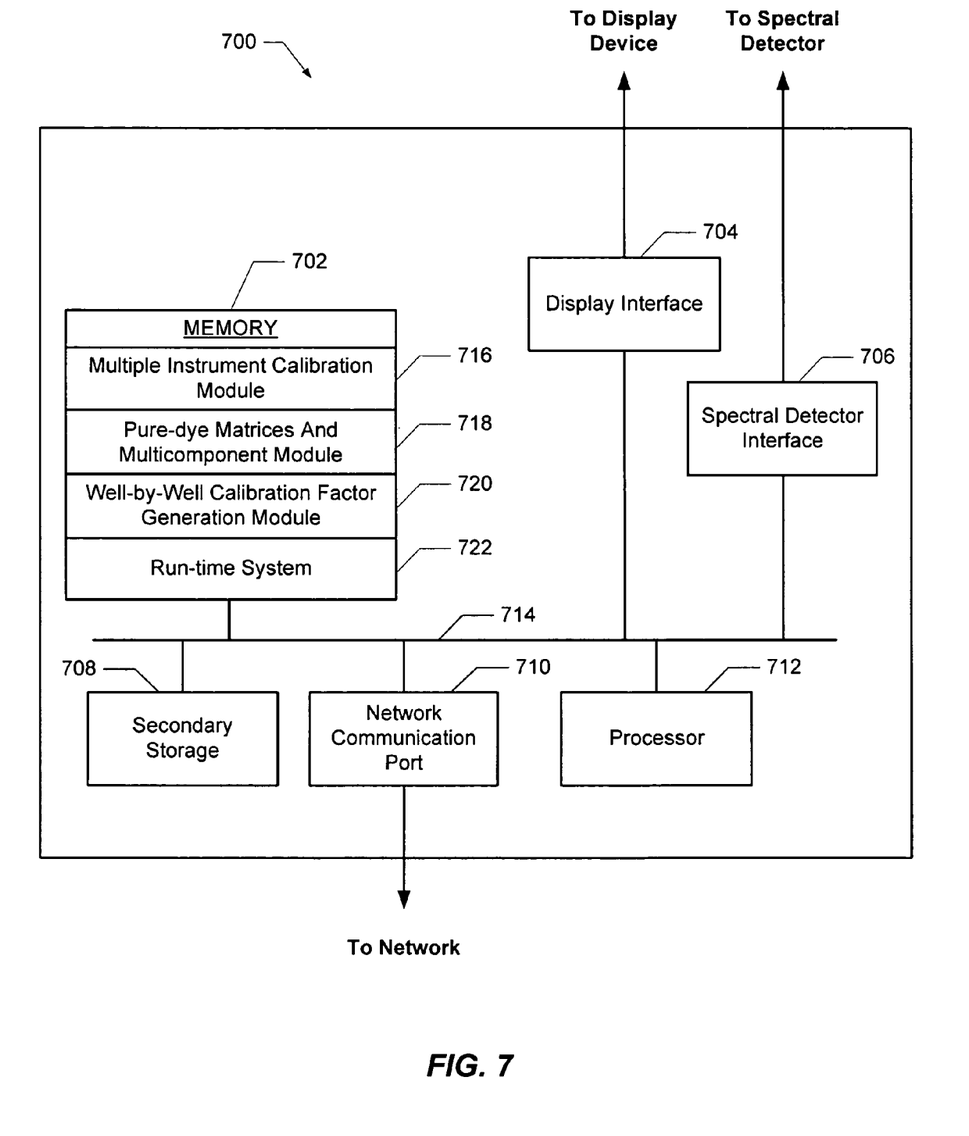
FIG. 7 is a block diagram of a system used in operating an instrument or methods in accordance with implementations of the present invention.

FIG. 7 is a block diagram of a system used in operating an instrument or method in accordance with implementations of the present invention. System 700 includes a memory 702 to hold executing programs (typically random access memory (RAM) or read-only memory (ROM) such as Flash), a display interface 704, a spectral detector interface 706, a secondary storage 708, a network communication port 710, and a processor 712, operatively coupled together over an interconnect 714.

Display interface 704 allows presentation of information related to operation and calibration of the instrument on an external monitor. Spectral detector interface 706 contains circuitry to control operation of a spectral detector including duplex transmission of data in real-time or in a batch operation. Secondary storage 708 can contain experimental results and programs for long-term storage including one or more pure-dye matrices, calibration factors and other data useful in operating and calibrating the spectral detector. Network communication port 710 transmits and receives results and data over a network to other computer systems and databases. Processor 712 executes the routines and modules contained in memory 702.

In the illustration, memory 702 includes a multiple instrument calibration module 716, pure-dye matrices and multicomponent module 718, a well-by-well calibration factor generation module 720 and a run-time system 722.

Multiple instrument calibration module 716 contains includes routines to calibrate one or more instruments according to a set of calibration factors. The calibration factors adjust the signal measurements for different instruments to accommodate for optical variations and normalize spectral sensitivities. It is possible to have a constant Ct between instruments and over time as the calibration factors are derived from a common reference calibration plate as previously described. While it is possible to use the same reference calibration plate, it is more practical to have a set of reference calibration plates created with known amounts of each dye, which is used as part of a calibration vector. For example, the calibration factors applied by multiple instrument calibration module 716 account for optical variations introduced by different well positions, optical paths and other related differences between instruments and over time on the same instrument.

Pure-dye matrices and multicomponent module 720 provides the data and routines to deconvolve the spectral contribution from the spectra of multiple spectral species. The pure-dye matrices contain the coefficients used to solve a set of simultaneous equations for determining the spectral species detected in a signal. In the dye-based calibration approach, each assay may require a different pure-dye matrix and an instrument with matching filters for the dye-based calibration approach to work properly. As an alternative, the filter-based calibration approach can apply a single calibration factor generated for the instrument to one or more pure-dye matrices corresponding to different assays. This latter filter-based approach is more cost-effective yet comparable in accuracy to the dye-based calibration approach. For example, the filter-based approach provides sufficient accuracy if variation in the measurement is due to plate seal variations.

Well-by-well calibration factor generation module 720 includes routines that calculate the calibration factors for each well and spectral species. In general, these routines compare an expected or predetermined signal response from one or more spectral species in a calibration plate with the detected or measured signal response as the one or more wells in the plate are scanned during calibration. The calibration plate provides a reference combination of spectral species having a known signal response. By using the same or similar calibration plate with the same combination of dye concentrations or reporters, a constant Ct can be used for comparison across different instruments or the same instrument over time.

Run-time system 722 manages system resources used when processing one or more of the previously mentioned modules. For example, run-time system 722 can be a general-purpose operating system, an embedded operating system or a real-time operating system or controller.

System 700 can be preprogrammed, in ROM, for example, using field-programmable gate array (FPGA) technology or it can be programmed (and reprogrammed) by loading a program from another source (for example, from a floppy disk, an ordinary disk drive, a CD-ROM, or another computer). In addition, system 700 can be implemented using customized application specific integrated circuits (ASICs).

Having thus described various implementations and embodiments of the present invention, it should be noted by those skilled in the art that the disclosures are exemplary only and that various other alternatives, adaptations and modifications may be made within the scope of the present invention. For example, it is mentioned that the calibration factors allow a constant Ct to be used across instruments and over time on the same instrument. However, it is also contemplated that calibrations performed in accordance with implementations of the present invention can also be performed to facilitate a constant Ct for different platforms and manufacturers as well and not necessarily on the same brand or line of instruments from a single manufacturer

Embodiments of the invention can be implemented in digital electronic circuitry, or in computer hardware, firmware, software, or in combinations thereof. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs.

Thus, the invention is not limited to the specific embodiments described and illustrated above. Instead, the invention is construed according to the claims that follow.

What is claimed is:

1. A computer implemented method of generating position-specific calibration factors for a spectral detector instrument, comprising:
   receiving a calibration plate comprising a plurality of wells, each at a different respective well position and each containing a plurality of spectrally distinguishable species;
   exposing the calibration plate to an excitation source that emits light and causes the plurality of spectrally distinguishable species in each of the plurality of wells to fluoresce;
   measuring a respective signal response associated with each spectral species at each respective well position in the calibration plate;
   comparing the respective measured signal response for each spectral species at each respective well position in the calibration plate with a predetermined signal response for each spectral species; and
   determining a respective calibration factor for each spectral species in each well in response to the comparing, to compensate for respective differences between the respective measured signal response for each spectral species at each respective well position and the predetermined signal response for each spectral species, wherein the calibration factors generated for each well compensate for variations in spectral responses due to many different angles of entry of the light into the different wells of the plurality and wherein a predetermined concentration of one or more probes includes a passive reference and the concentration of each probe is determined with respect to the passive reference.

2. The method of claim 1 further comprising:
   reusing the same calibration plate to generate a respective calibration factor for each well and spectral species for one or more different instruments in a single platform.

3. The method of claim 1 further comprising:
   reusing the same calibration plate to generate a respective calibration factor for each well and spectral species for one or more different instruments from more than one different platform.

4. The method of claim 3, wherein one dye is used as a passive reference to normalize the spectral species in each well of the calibration plate.

5. The method of claim 1 further comprising:
   reusing the same calibration plate to generate a respective calibration factor for each well and spectral species for one instrument over time.

6. The method of claim 1, wherein the calibration plate is selected from a set of plates including a 96-well plate, a 384-well plate, and a plate having a multiple of 96-wells.

7. The method of claim 1, wherein the spectral species includes one or more dyes selected from a set including: FAM, SYBR Green, VIC, JOE, TAMRA, NED, CY-3, Texas Red, CY-5, Hex, and ROX.

8. The method of claim 1 wherein the excitation source is selected from a set of excitation sources including: a laser device, a halogen lamp, an arc lamp, an organic LED, and an LED device.

9. The method of claim 1 wherein the measuring the respective signal response further comprises:
   performing a multicomponent analysis on the respective signal response at each respective well position to identify the contribution from each spectral species to the respective signal; and
   deconvolving the contribution from the spectral species associated with an excitation filter filtering the respective signal response.

10. The method of claim 1 wherein the measuring the respective signal response further comprises:
    using the respective signal response directly as a measure of the spectral species that corresponds to an excitation filter filtering the respective signal response.

11. A method of calibrating a spectral detector instrument position specifically comprising:
    receiving a plate comprising a plurality of wells, each at a different respective well position, and containing one or more potential targets and a plurality of spectrally distinguishable species in each well of the plate;
    exposing each well in the plate to an excitation source that emits light and causes one or more of the plurality of spectrally distinguishable species to fluoresce in correlation to the presence of the one or more of the one or more potential targets;
    measuring the initial signal values received from the plurality of spectrally distinguishable species at each of the different respective well positions; and
    adjusting the respective initially measured signal values using respective calibration factors for each well position and each of the spectrally distinguishable species, each of the calibration factors being derived from a calibration plate having predetermined relative concentrations of each of the plurality of spectrally distinguishable species, wherein the respective calibration factors compensate for respective differentials between a respective measured signal response in the calibration plate compared with a predetermined signal response for each of the plurality of spectrally distinguishable species, and the calibration factors generated for each well compensate for variations in spectral responses due to many different angles of entry of the light into the different wells of the plurality and wherein a predetermined concentration of one or more probes includes a passive reference and the concentration of each probe is determined with respect to the passive reference.

12. The method of claim 11 further comprising:
    directly using the adjusted respective initially measured signal values collected from multiple instruments in an experiment.

13. The method of claim 12, wherein the respective initially measured signal values are collected over time from each of the multiple instruments.

14. The method of claim 11, wherein the plate containing one or more potential targets and the calibration plate is selected from a set of plates including a 96-well plate, a 384-well plate, and a plate having a multiple of 96-wells.

15. The method of claim 11, wherein the plurality of spectral species includes one or more probes selected from: FAM, SYBR Green, VIC, JOE, TAMRA, NED, CY-3, Texas Red, CY-5, and ROX.

16. The method of claim 15, wherein one of the plurality of spectral species comprises ROX used as a passive reference.

17. An apparatus for generating position-specific calibration factors for a spectral detector instrument, comprising:
  means for receiving a calibration plate comprising a plurality of wells, each at a different respective well position, and containing a plurality of spectrally distinguishable species in each of the plurality of wells;
  an excitation source configured to expose calibration plate to light to cause the plurality of spectrally distinguishable species in each of the plurality of wells to fluoresce;
  a detector configured to measure a respective signal response associated with each spectrally distinguishable species at each respective well position of the calibration plate;
  a processor configured to:
    compare the respective measured signal response for each spectrally distinguishable species at each respective position of the plurality of wells in the calibration plate with a predetermined signal response for each spectrally distinguishable species; and
    determine a respective calibration factor for each well and each spectrally distinguishable species in response to the comparison to compensate for respective differences between the respective measured signal response and the predetermined signal response, wherein the calibration factors generated for each well compensate for variations in spectral responses due to many different angles of entry of the light into the different wells of the plurality and wherein a predetermined concentration of one or more probes includes a passive reference and the concentration of each probe is determined with respect to the passive reference.

18. A non-transitory computer-readable medium instructions, executable by a processor, the instructions comprising instructions for:
  receiving a plate comprising a plurality of wells, each well of the plate having a different respective well position and containing one or more potential targets and a plurality of spectrally distinguishable species;
  exposing each well in the plate to an excitation source that emits light and causes the spectrally distinguishable species to fluoresce in correlation to the presence of one or more of the one or more potential targets;
  measuring the respective initial signal values received from each of the spectrally distinguishable species in each of the respective well positions of the plate; and
  adjusting the respective initially measured signal values using a respective calibration factor for each well position and each different spectrally distinguishable species from a calibration plate having predetermined relative concentrations of the one or more spectrally distinguishable species, wherein the respective calibration factors compensate for respective differentials between a respective measured signal response in the calibration plate compared with a predetermined signal response for each of the spectrally distinguishable species, and compensate for variations in spectral responses due to many different angles of entry of the light into the different wells of the plurality and wherein a predetermined concentration of one or more probes includes a passive reference and the concentration of each probe is determined with respect to the passive reference.

* * * * *